United States Patent
Dasgupta et al.

(10) Patent No.: US 7,632,404 B2
(45) Date of Patent: Dec. 15, 2009

(54) BARRIER WITH A SEATED ION EXCHANGE BEAD AND METHOD

(75) Inventors: Purnendu K. Dasgupta, Arlington, TX (US); Bingcheng Yang, Arlington, TX (US); Kannan Srinivasan, Tracy, CA (US); Masaki Takeuchi, Tokushima (JP)

(73) Assignees: Dionex Corporation, Sunnyvale, CA (US); Board of Regents, The Univesity of Texas System, Austin, TX (US)

( * ) Notice: Subject to any disclaimer, the term of this patent is extended or adjusted under 35 U.S.C. 154(b) by 0 days.

(21) Appl. No.: 11/940,892

(22) Filed: Nov. 15, 2007

(65) Prior Publication Data

US 2009/0127200 A1   May 21, 2009

(51) Int. Cl.
*B01D 15/08* (2006.01)
*C25B 1/16* (2006.01)
*G01N 27/00* (2006.01)
*C02F 1/28* (2006.01)
*C25D 17/00* (2006.01)

(52) U.S. Cl. .................... 210/198.2; 210/656; 204/194; 204/647; 205/512

(58) Field of Classification Search .............. 210/198.2, 210/656; 204/601, 605, 451, 455, 647; 205/512
See application file for complete search history.

(56) References Cited

U.S. PATENT DOCUMENTS

| | | | |
|---|---|---|---|
| 2,903,406 | A | 9/1959 | Miller |
| 4,187,333 | A | 2/1980 | Rembaum et al. |
| 4,253,900 | A | 3/1981 | Dege et al. |
| 4,500,430 | A | 2/1985 | Dasgupta |
| 4,647,380 | A | 3/1987 | Dasgupta |
| 4,999,098 | A | 3/1991 | Pohl et al. |
| 5,045,204 | A | 9/1991 | Dasgupta et al. |
| 5,352,360 | A | 10/1994 | Stillian et al. |
| 6,225,129 | B1 | 5/2001 | Liu et al. |
| 6,325,976 | B1 | 12/2001 | Small et al. |
| 6,682,701 | B1 | 1/2004 | Liu et al. |
| 6,716,629 | B2 * | 4/2004 | Hess et al. .................. 435/420 |
| 2003/0127392 | A1 | 7/2003 | Srinivasan et al. |
| 2003/0132163 | A1 | 7/2003 | Srinivasan et al. |
| 2005/0173346 | A1 * | 8/2005 | Srinivasan et al. .......... 210/656 |

(Continued)

FOREIGN PATENT DOCUMENTS

WO   WO 2004/024302 A1   3/2004

OTHER PUBLICATIONS

Strong, DL, PK Dasgupta, K Friedman, J Stillian. Electrodialytic eluent production and gradient generation in ion chromatography, *Anal. Chem* 63:480-486 (1991).

(Continued)

*Primary Examiner*—Krishnan S Menon
*Assistant Examiner*—Katherine Zalasky
(74) *Attorney, Agent, or Firm*—Morgan, Lewis & Bockius LLP; David J. Brezner (57) ABSTRACT

Ion transport apparatus (e.g. an electrolytic eluent generator or a suppressor for ion chromatography) in which ions in a first chamber are transported to a liquid in second chamber through a wall comprising an ion exchange bead sealed in a bead seat. The wall is capable of transport ions but of substantially blocking bulk liquid flow.

30 Claims, 7 Drawing Sheets

U.S. PATENT DOCUMENTS

2006/0057733 A1     3/2006    Liu et al.
2006/0211125 A1     9/2006    Liu et al.

OTHER PUBLICATIONS

Strong, DL, PK Dasgupta. Electrodialytic production of gas-free sodium hydroxide based on Donnan breakdown, *J. Membr. Sci.* 57:321-336 (1991).

Strong, DL, CU Joung,, PK Dasgupta. Electrodialytic eluent generation and suppression, ultralow background conductance suppressed anion chromatography, *J. Chromatogr.* 546:159-173 (1991).

Liu, Y, N Avdalovic, C Pohl, R Matt, H Dhillon and R Kiser. An on-line, high-purity acid and base eluent generation system for ion chromatography, *Am. Lab.*, Nov. 1998, pp. 48C-54C.

Sjögren, A, CB Boring, PK Dasgupta, JN Alexander. Capillary ion chromatography with on-line high-pressure electrodialytic NaOH eluent production and gradient generation, *Anal. Chem.* 69:1385-1391 (1997).

Dasgupta, PK, RQ Bligh, J. Lee, V. D'Agostino. Ion penetration through tubular ion exchange membranes, *Anal. Chem.* 57:253-257 (1985).

Berglund, I, PK Dasgupta, JL Lopez, O. Nara. Two-dimensional conductometric detection in ion chromatography: Sequential suppressed and single column detection, *Anal. Chem.* 65:1192-1198 (1993).

Sjögren, A, PK Dasgupta. Two-dimensional conductometric detection in chromatography. Analyte identification, quantitation of very weak acid anions, and universal calibration, *Anal. Chem.* 67:2110-2118 (1995).

Sjögren, A, PK Dasgupta. A planar microelectrodialytic NaOH generator for eluite conversion after suppressed conductometric detection in ion chromatography, *Anal. Chim. Acta* 384:135-141 (1999).

Boring, CB, PK Dasgupta, A Sjögren. Compact, field-portable capillary ion chromatograph, *J. Chromatogr.* 804:45-54 (1998).

Small, H, Y. Liu, N. Avdalovic. Electrically polarized ion-exchange beds in ion chromatography: eluent generation and recycling, *Anal. Chem.* 70:3629-3635 (1998).

Liu, Y, K Srinivasan, C Pohl, N. Avdalovic. Recent developments in electrolytic devices for ion chromatography, *J. Biochem. Biophys. Methods* 60:205-232 (2004).

Pyo, D, PK Dasgupta, LS Yengoyan. High temperature open tubular capillary column ion chromatography, *Anal. Sci.* 13 (Suppl): 185-190 (1997).

Kubáň, P, B. Karlberg, P Kubáň, V Kubáň. Application of a contactless conductometric detector for the simultaneous determination of small anions and cations by capillary electrophoresis with dual-opposite end injection, *J. Chromatogr. A* 964:227-241 (2002).

Kubáň, P, PK Dasgupta, CA Pohl. Open tubular anion exchange chromatography. Controlled layered architecture of stationary phase by successive condensation polymerization, *Anal. Chem.* 79:5462-5467 (2007).

Yang, B, M Takeuchi, PK Dasgupta, T. Umemura, Y Ueki, K Tsunoda. Tailoring elution of tetraalkylammonium ions. Ideal electrostatic selectivity elution order on a polymeric ion exchanger, *Anal. Chem.* 79:769-772 (2007).

Ueki, Y, T. Umemura, J Li, T Odake, K Tsunoda. Preparation and application of methacrylate-based cation-exchange monolithic columns for capillary ion chromatography, *Anal. Chem.* 76:7007-7012 (2004).

Yang, B., et al. On-line gas-free electrodialytic eluent generator for capillary ion chromatography. *Anal. Chem.* 80:40-47 (2008).

\* cited by examiner

Array of single beads – top view

Figure 3a

Array of single beads – side view

BARRIER WITH A SEATED ION EXCHANGE BEAD AND METHOD

BACKGROUND OF THE INVENTION

The present invention relates to an ion transport barrier, particularly one used for an ion transport device such as one for generating a high-purity acid, base, or salt or for a suppressor in an ion chromatography system.

In liquid chromatography, a liquid sample containing a number of components to be separated is directed through a chromatography separator, typically an ion exchange resin bed. The components are separated on elution from the bed in a solution of eluent. One form of liquid chromatography is referred to as ion chromatography. In this known technique, ions to be detected in the sample, consisting of ions in an aqueous solution, are separated in a chromatography separator, such as a chromatography column, using an eluent containing an acid or a base and, thereafter, sent to a suppressor, followed by detection, typically by an electrical conductivity detector. In the suppressor, the electrical conductivity of the electrolyte is suppressed but not that of the separated ions, so that the latter may be detected by the conductivity detector. One such suppressor, disclosed in U.S. Pat. No. 6,325,976, is continuous and electrolytic. Suppression is in a packed bed of ion exchange resin. Other suppressors are disclosed in U.S. Pat. Nos. 4,999,098, 4,500,430, 4,647,380 and 5,352,360. There, the suppressor is in the form of a membrane suppressor in which a regenerant solution flows on one side of an ion exchange membrane and the sample stream flows on the other side. Suppression occurs by transport of electrolyte ions of opposite charge to the sample ions in the eluent across the membrane and into the regenerant solution. Thus, the suppressor serves as an ion transport apparatus.

A convenient source of high-purity acid, base, or salt for use as an eluent for liquid chromatography and, particularly, for ion chromatography is disclosed in U.S. Pat. Nos. 5,045,204 and 6,225,129. As disclosed, for the generation of a base or acid, a cation or anion source is disposed in a flowing or non-flowing cation or anion source reservoir. An aqueous liquid flows through a base- or acid-generation chamber separated from the source reservoir by an ion exchange barrier, in the form of an ion exchange membrane, substantially blocking liquid flow across it while providing a cation or anion transport bridge. Electrical potential is applied to electrolytically generate hydroxide or hydronium ions in the base or acid generation chamber. Thus, like the suppressor of U.S. Pat. No. 5,352,360, the acid or base generation apparatus of U.S. Pat. No. 6,225,129 or 5,045,204 or devices described in US Patent Application 20060211125 are ion transport apparatus in which ions are transported across an ion exchange membrane.

There would be an advantage for providing a form of ion transport barrier in such prior art ion transport apparatus which has improvements over the ion exchange membrane of such ion transport apparatus.

SUMMARY OF THE INVENTION

In one embodiment of the present invention, an ion transport barrier is provided comprising a wall with a bead seat and an ion exchange bead sealed in the bead seat. The bead is capable of passing ions of one charge, positive or negative, and of substantially blocking bulk liquid flow.

In another embodiment of the present invention, ion transport apparatus is provided in which ions of one charge, positive or negative, in a liquid in a first or second chamber are transported to a liquid in the other of the first or second chambers through a barrier which blocks bulk liquid flow between the first and second chambers. The apparatus comprises a first chamber and an adjacent second chamber having an inlet and an outlet, and a first wall separating said first and second chambers. The first wall comprises a first ion exchange bead sealed in a first bead seat in said first wall. The first ion exchange bead is capable of passing ions of one charge, positive or negative, and of blocking bulk liquid flow.

Specific ion transport apparatuses include electrolytic eluent generator and a suppressor for ion chromatography. One embodiment of a suppressor comprises an ion receiving flow channel and an adjacent liquid sample flow-through channel having an inlet and an outlet, and a first wall separating said ion receiving flow channel and said sample flow-through channel. The first wall comprises a first ion exchange bead sealed in a bead seat in said first wall, said first ion exchange bead being capable of passing ions of one charge, positive or negative, and of blocking bulk liquid flow.

In another embodiment of the invention, a method is provided which includes transporting ions of one charge, positive or negative, in a liquid in a first chamber to liquid in a second chamber through a barrier which blocks liquid flow between the first and second chambers. The method comprises providing a first ion source containing a selected ion of one charge, positive or negative, in a first chamber, flowing an ion receiving liquid stream through an ion receiving flow channel adjacent said first chamber, and providing a first wall separating said first chamber from said ion receiving flow channel, said first wall comprising a first ion exchange bead sealed in a bead seat in said first wall. The selected ion is transported from said ion source to said flowing ion receiving stream through the first ion exchange bead.

Such method can be for suppression of a liquid for ion chromatography or as a method for generating an acid or a base. One embodiment of a suppression method comprises providing an ion receiving flow channel and an adjacent liquid sample flow-through channel having an inlet and an outlet, providing a first wall separating said ion receiving flow channel and said sample flow-through channel. The first wall comprises a first ion exchange bead sealed in a bead seat in said first wall. The first ion exchange bead is capable of passing ions of one charge, positive or negative, and of blocking bulk liquid flow. A sample solution including sample ions of one charge, positive or negative, which have been chromatographically separated in an eluent including selected ions of opposite charge to said sample ions, flows through said liquid sample flow-through channel. The selected ions are suppressed by transporting said selected ions from said sample stream flow channel through said first ion exchange bead into said ion receiving flow channel.

Another embodiment is an electrolytic method for generating an acid or a base. The method comprises providing an anion or a cation source in an aqueous liquid in an anion or cation source reservoir in a first chamber, and flowing an aqueous liquid stream through an acid or base generation chamber which is separated from the anion or cation source reservoir by a first wall separating said first chamber and said acid or base generation flow-through channel. The first wall comprises a first ion exchange bead sealed in a bead seat in said first wall. The first ion exchange bead is capable of passing ions of one charge, positive or negative, and of substantially blocking bulk liquid flow. An electrical potential is applied between said anion or cation source reservoir and said acid or base generation chamber, respectively, through said ion exchange bead. The anion or cation from said anion or cation source reservoir is transported through said first ion exchange bead into said acid or base generation chamber to electrolytically generate an acid, base, or salt.

BRIEF DESCRIPTION OF THE DRAWINGS

FIG. 4b is an enlarged cross-sectional view of one bead in a bead seat of the bead array barrier of FIG. 4a.

DETAILED DESCRIPTION OF PREFERRED EMBODIMENTS

Method and apparatus of the present invention are applicable to ion transport apparatus and methods, particularly ones for generating a chromatography eluent and for ion chromatography suppression such as set forth above, specifically by replacing an ion exchange membrane barrier with a wall seating an ion exchange bead. Also, it is applicable to generation of an eluent for liquid chromatography other than ion chromatography which does not use a suppressor and which uses a different detector, e.g. an ultraviolet (UV) detector. The eluent may be in a form (e.g., salt) other than an acid or base. Thus, the term "aqueous stream" includes pure water or water with such additives. Also, the terms "eluent comprising a base," "eluent comprising an acid," an "acid" or a "base" meets an aqueous stream including acid or base generated in the ion transport apparatus and combinations thereof. As set forth above, the method and apparatus of the present invention are also applicable to a suppressor, and other electrolytic devices such as eluent purifier (US Patent Application 20030127392) or aqueous stream purifier (US Patent Application 20030132163), and the like. For simplicity of description, the present system will first be described with respect to a system for generating a high-purity base. It should be understood that by the appropriate change of reagents and polarities of the electrodes, the system is also applicable to the generation of high-purity acid.

The system is first described with respect to the generation of a base suitable for use as an eluent in the analysis of anions in a chromatographic separator, such as a chromatography column packed with anion exchange resin. In this instance, the generated base typically is an alkali-metal hydroxide, such as sodium or potassium hydroxide, for analysis of anions. For analysis of cations, the eluent generated would be an acid such as methanesulfonic acid.

As illustrated in U.S. Pat. No. 6,225,129, one way of electrodialytically generating a hydroxide eluent, e.g., KOH, uses a substantially stationary or non-flowing stream of KOH on one side of an ion exchange barrier. An electrode, e.g., formed of a metal, e.g. a noble metal, functioning as an anode in electrical communication with the KOH solution, preferably is disposed in the solution. The KOH solution is separated from the other side by a cation exchange membrane (CEM) or a stack of CEMs (for mechanical stability in high-pressure application). Aqueous solutions, preferably purified water, flows on the other side of the CEM. Under the electric field, K ions move across the membrane, according to the principle illustrated in the '129 patent.

In the present invention, a barrier comprising a wall with an ion exchange bead in a bead seat or a barrier comprising an array of beads replaces the ion exchange membrane, e.g. in the devices of the '129 or '976 patents. Also, the source of anions or cations can be a flowing stream as set forth in the '204 patent.

Principles of operation of the '129 and '204 patents are applicable to the present invention. Electrodialytic generation of a hydroxide eluent, say KOH, is performed using a stationary or flowing stream of KOH on one side and an ion exchange barrier with a noble metal electrode, functioning as an anode, disposed therein in electrodialytic eluent generators (EDGs). The KOH solution is separated from the other side by the cation exchange barrier. Pure water flows into the other side where a negative electrode is disposed. Under the electric field, $K^+$ moves across the membrane, the cathode reaction being $$K^+ + H_2O + e^- \rightarrow KOH + \tfrac{1}{2}H_2 \qquad (1)$$

While oxygen is produced at the anode:

$$2OH^- - 2e^- \rightarrow H_2O + \tfrac{1}{2}O_2 \qquad (2)$$

On the anode side, it is possible to use any $K^+$ compound as a $K^+$ source; it does not have to be KOH. However, the Donnan barrier that prevents negative ions to be transported across a cation exchanger bearing fixed negative sites is not absolute. If the concentration gradient is high enough, some Donnan-forbidden leakage may occur. For example, if $K_3PO_4$ is used as the electrolyte, some penetration of phosphate into the generated eluent may occur. It is for this reason KOH is the preferred electrolyte to generate KOH. Prior art EDGs use a single (or stacked, effectively functioning as a thick single membrane) membrane. They have also been used for the generation of small but constant amounts of base, to be used in two-dimensional conductivity detection. These generators have the virtue of near-unity Faradaic Efficiency E, E being given by $$E = \left[ \frac{1608\, CQ}{i} \right] \qquad (3)$$

Where a current of i nA generates C mM product KOH flowing at Q μL/min. They do have the distinct disadvantage of the product being accompanied by copious amounts of gas, in this case $H_2$ (and for a generated acid eluent, $O_2$), which must be removed. Porous polypropylene and polytetrafluoroethylene (PTFE) membranes, typically in tubular form, have been used for gas removal when the EDG is on the low pressure side of the pump. An eluent EDG that is on the high pressure side of the pump is preferred because in that case the pump needs to pump only water. When generating gradients, the high pressure placement eliminates potentially significant delay volume within the pump and ancillary components such as mixers. However, this requires that gas removal now be accomplished under high pressure. Porous membranes cannot be used for this purpose. For gas removal under high pressure, the use of permeable wall capillaries that can withstand high pressure, such as those made of polystyrene, PTFE and various other fluorocarbons such as Teflon AF® and polypropylene, etc. are possible. The dimensions of such capillaries preferably are optimized to maximize gas removal and minimize the delay volume. Therefore, such devices which can directly produce the eluent in a gas-free manner would be desirable, especially if they can operate under high pressure.

According to one aspect of the present invention, an ion transport barrier is provided which includes a wall with a bead seat and an ion exchange bead sealed in the bead seat. The bead is capable of passing ions of one charge, positive or negative, and of substantially blocking bulk liquid flow. As used herein, substantially blocking means blocking all flow except a small amount of liquid leakage. Preferably, essentially all bulk liquid flow is blocked. The invention will be described first with respect to an ion transport apparatus including the ion transport barrier.

In one embodiment of the ion transport apparatus in the form of an acid or a base eluent generator, ions of one charge, positive or negative, e.g. $K^+$ ion, in an aqueous liquid in a first chamber are transported to an aqueous liquid in a second chamber through a barrier which prevents ion flow but which blocks bulk liquid flow. In the system of the '129 patent, the first chamber serves as an ion source chamber, and the second chamber includes a flowing aqueous solution, typically a flowing purified water stream. According to the present invention, instead of the ion exchange membrane, the barrier is a wall separating the first and second chambers which comprises at least a first ion exchange bead sealed in one or more bead seats. The ion exchange bead is in fluid communication with the ion source liquid in the first chamber and with the aqueous liquid in the second eluent generation chamber and is capable of passing positive or negative ions and of blocking bulk liquid flow. Preferably, a first electrode is in electrical communication with the ion source (first) chamber and a second electrode of opposite charge is in electrical communication with the solution in the eluent generation (second) chamber in which the acid or base eluent is generated. Preferably, the second chamber is of an elongate generally tubular configuration, specifically a capillary conduit. The ion exchange bead is particularly effective for use in a high pressure system for the second chamber, and one of small dimensions, such as a capillary conduit. The bead is preferably of spherical shape. Other shapes are possible provided the bead is sealed in the bead seat. The present invention also describes an array of bead configuration.

Figure 1:
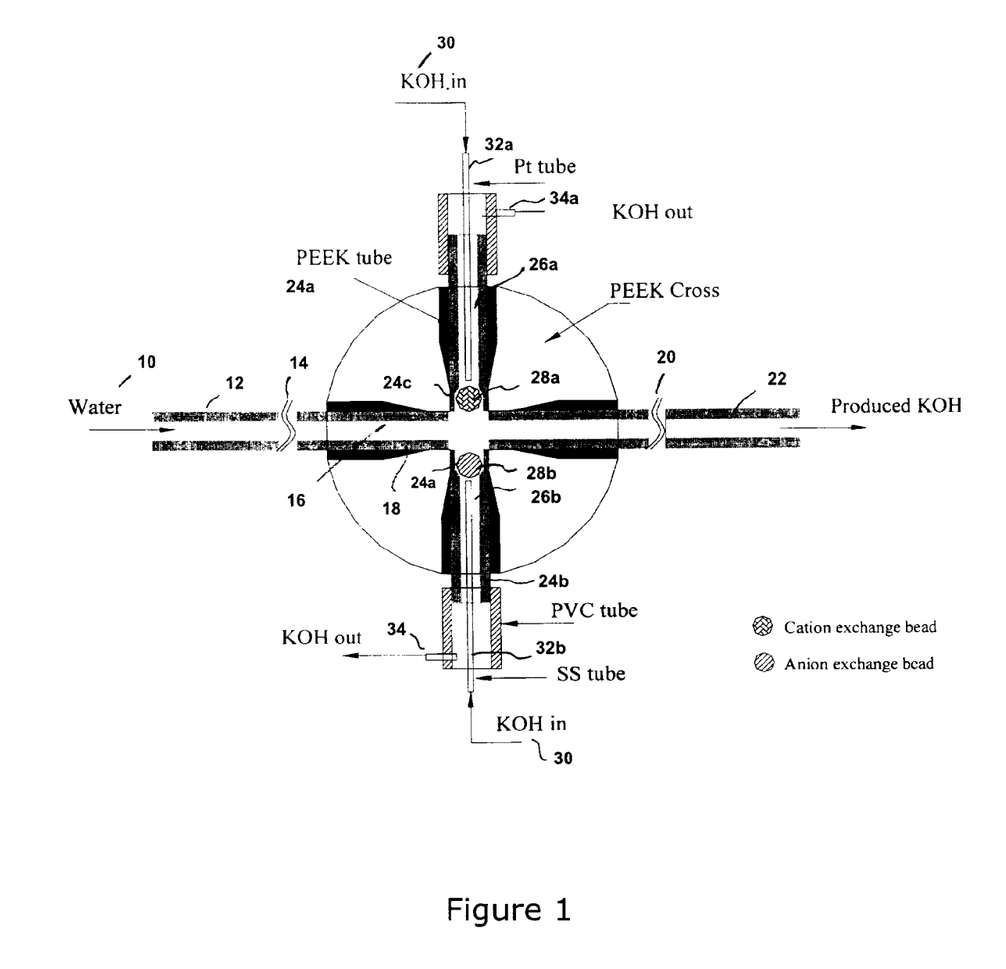
FIGS. 1 and 2 are schematic representations of ion transport apparatus according to the invention.

Referring to FIG. 1, one embodiment of an electrodialytic generator according to the present invention is illustrated which is very effective for use in producing an eluent in a high-pressure system, e.g. greater than about 100 psi, or greater than about 1000 psi, 5000 psi or more. This system includes a source of purified aqueous liquid, preferably deionized (DI) water 10, which flows through a conduit, tubing 12, with suitable connector 14 to flow-through eluent generation chamber 16 in cylindrical conduit or tubing 18 connected by suitable connector 20 to an outlet conduit, tubing 22. Tubes 24a and 24b define ion source reservoirs 26a and 26b, respectively, terminating at one end with outlets adjacent to chamber 16. Disposed between chamber 16 and chambers 26a and 26b are ion exchange bead 28a and 28b, respectively, of the same or opposite charge. Bead 28a is in fluid communication with chamber 26a and chamber 16, while bead 28b is in fluid communication with chamber 26b and chamber 16. The ion exchange beads are capable of passing ions of one charge, positive or negative, and of blocking bulk liquid flow. Beads 28a and 28b are sealed in cavities or bead seats 24c and 24d in the form of recesses in the portion of tubes 24a and 24b adjacent to tube 18. In this embodiment the combination of the beads and the surrounding interior walls of conduits 24a and 24b are bead seats 24c and 24d forming liquid seal.

As defined herein, the term "wall" encompasses a wall or wall portion defining a bead seat or seats in which a bead or beads are sealed. For use in an ion transport device, the wall is sealed at its periphery to the interior of the device to block bulk liquid flow around the wall. Other embodiments of walls according to the invention could include walls of any configurations such as a flat or curved sheet-like walls, or the interior wall of a conduit such as a tube.

Preferably, the walls are inert, not electrical conductive, and do no swell substantially due to hydration. Preferred substrates include substantially non-swellable plastic or non-swellable polymer materials such as polypropylene, polyethylene, PEEK, PTFE and the like. The thickness of the substrate material typically is less than 5000 microns (µm), preferably less than 1000 microns, and more preferably less than 500 microns. The bead seat opening typically are less than 5000 microns in diameter for a round opening and of comparable cross-section for an opening of another shape, preferably less than 1000 microns and more preferably less than 500 microns. The bead seat recesses can be of any shape so long as the ion exchange bead is tightly held in the recess without any substantial leaks. The bead seat recesses can be machine drilled. Also, the bead seat recesses may be formed as a counter-sunk bore, or of semi-spherical shape. Additionally the wall may be injection molded in the form of a substrate sheet or other configuration, with the required bead seat configuration. In the molded version appropriate details to the hardware may be integrated to ensure that the bead is entrapped in the bead seat recess in a check valve type configuration. Other modes of sealing may be used.

One way to form the seal is to insert the bead in a dry form in bead seats 24c and 24d in the tubing. Then the bead is wetted to expand and form a tight seal within the tubing, preferably formed of a rigid, electrically non-conducting (e.g. plastic) material such as PEEK. The bead is trapped in the bead seat and exposed to liquids on both sides. Such an assembly functions as a ball-in-seat check valve since flow would ensure a tight seal between the bead and the surface of the tube in which it is seated. In one embodiment, the dry bead expands in place when contacted with liquid to ensure a tight fit. Also, it is possible to shrink the bead and then to expand it when in the bead seat. For example, anion exchange resin beads could be put into a shrunken nitrate form and then converted to the hydroxide form to expand and provide a physical seal against the cavity. Similarly, for cation exchange resin beads the sodium form may be converted to hydronium form, resulting in an expansion of the beads that can be used to make a seal against the PEEK cavity.

It is also possible to use thermal sealing techniques around the bead to seal against the bead seat. For example using a polyethylene or polypropylene wall, application of heat around the perimeter of the bead seat could melt the adjacent polymer wall. The adhesion of the melted polymer wall with the resin bead upon cooling would result in a seal against the perimeter of the bead seat. Adhesives such as silicone glue around the perimeter may also be used for sealing. Another approach would be to form the ion exchange bead resin in situ in the polymer wall via conventional polymerization approach. In this case a template to define the bead shape could be used. The wall defining the bead seat, e.g. a polymer wall, would preferably be selected not to react with the resin synthesis reagents or chemicals.

Suitably, the resin beads are of a generally spherical form and can be of the type and size used for resin beds used in a variety of applications from chromatography to water purification. Preferably, the beads are cross-linked to a sufficient extent to provide structural strength, e.g. at least 2%, more preferably at least about 8% and to as high as 50% or more. The beads are ion exchange materials. Such materials are well known in the prior art and are typically polymer based for example styrene divinylbenzene based cross-linked resin and the like.

There are significant advantages of the present approach. For example, in the present single bead or an array of bead configuration swelling occurs only in the interstitial holes in the bead seats. Therefore, when using a polymer wall it is preferable that the wall does not show any substantial expansion or contraction. This provides a significant handling advantage compared to an ion exchange membrane. Conventional ion exchange membranes swell when wet and the membrane becomes slippery, which may result in difficulties in handling of the membrane. Additionally when used in devices such as water purifiers, the membrane dimensional can change due to swelling which can affect the device assembly and performance. For example, with conventional ion exchange membranes, when assembling in the wet configuration, the membranes may need to be resized for dimensional change after wetting. This is an added step in the assembly process. When assembled dry proper precautions should be taken to ensure that there are no big variance in the moisture content as this will affect the dimensions of the ion exchange membrane.

Another advantage of the present invention over ion exchange membranes is avoiding the influence of such swelling on membrane performance. For example, when suppressor membranes are too dry and are assembled, the swelling forces may result in increasing the device internal back pressure due to the expansion of the membrane. Higher internal pressures in suppressor devices or water purifier devices are not desirable as this can cause these devices to leak. By selectively allowing ion transport through ion exchange beads in specific regions in the wall of the present invention, the above problems of ion exchange membranes are minimized or overcome.

A device built with the single bead or array of bead configuration shows high resiliency under high pressure conditions. In contrast, devices built with conventional ion exchange membranes can leak and show poor pressure resiliency.

In one embodiment, the resin beads of the present invention are preferably slightly smaller than the bead seat holes when the sealing occurs via swelling of the beads. When press fitting the resin in the cavity the resin bead can be slightly larger than the bead seat recesses. It is also possible to use large resin bead and only expose a small portion of the resin surface via the bead seat. This can be used when the resin is held in place by sealing against the bead seat perimeter, e.g. by the application of heat as described above.

The resin beads are preferably substantially spherical although other shapes may be used. They are typically less than 5000 microns nominal diameter; preferably less than 1000 microns, and more preferably less than 500 microns for use in some devices such as microdevices, e.g. when seated in a capillary tube. The rate of ion transport through the ion exchange bead or beads in a wall can be controlled by the ratio of the exposed surface area of the beads relative to the wall in which the beads are seated. Depending on the desired degree of ion transport, it is preferable that the ratio of exposed bead surface area to the surface area of the exposed surrounding wall containing the bead seats be at least 1:1, more preferably at least 2:1, and most preferably at least 5:1 to 10:1 or more.

In one embodiment, the ion source 30, e.g., KOH in an aqueous solution, flows through the interior of electrically conductive (metal) tubes 32a and 32b disposed in chambers 26a and 26b to direct the KOH solution to outlets in chambers 26a and 26b close to beads 28a and 28b, respectively. The KOH solution flows out of tubes 32a, and 32b through outlet tubes 34a and 34b, respectively. Tubes 32a and 32b also serve as electrodes of opposite polarity and are connected to a power source, not shown. During operation, an electric current flows between chambers 26a and 26b through chamber 16. In another embodiment, not shown, the ion source is ion exchange medium such as an ion exchange bed in an aqueous solution.

In an alternative embodiment, not shown, only one ion source chamber 26a and one bead 24c are used. There, the second electrode is in communication with the eluent generating chamber, preferably in contact with solution therein.

Figure 2:
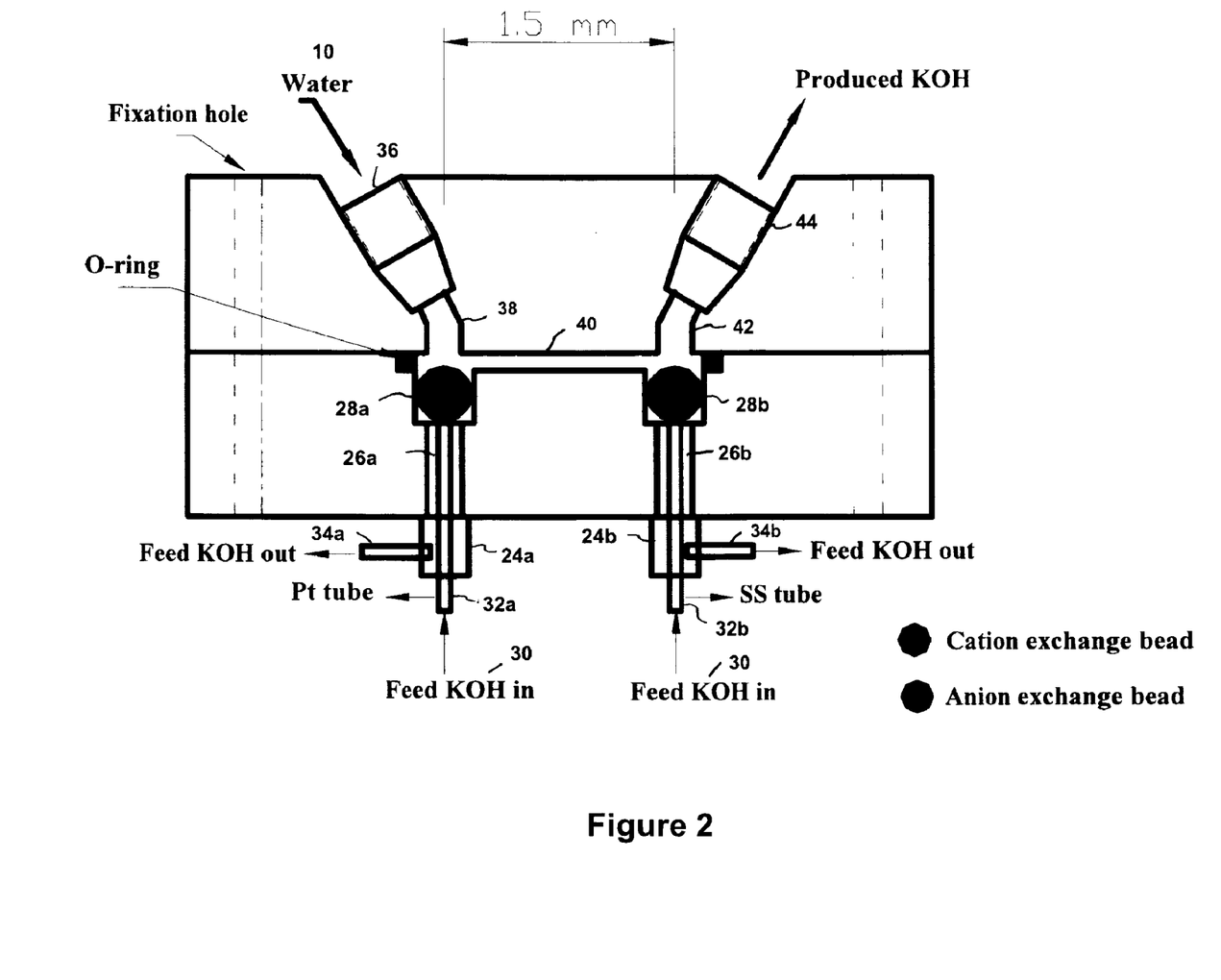

Another embodiment is illustrated in FIG. 2 in which the two beads are side by side within the same horizontal plane. Like parts will be designated with like numbers. Bead 28a is a cation exchange bead, and bead 28b is an anion exchange bead. In this system, the water flows into an inlet tube 36 at the top of the device through conduit 38 across conduit 40 and the produced KOH flows up conduit 42 and out conduit 44. This embodiment has the advantage that it is easily modified to accommodate multiple resin beads or bead arrays as will be described hereinafter.

In other embodiments similar to the configurations of FIGS. 1 and 2, an array of beads is used seated in multiple seats in a wall which can be of a generally flat or curved sheet-like configuration. A flat configuration of the array of beads configuration is shown in FIGS. 3a and 3b and 4a and 4b. In a preferred configuration, the exposed surface of one bead is arranged in close proximity to or in contact with other exposed bead surfaces in their respective seats. The resulting configuration produces a functional sheet-like (e.g. thin-film) ion exchange surface analogous to an ion exchange membrane as used in prior art ion transport devices. Advantages of the bead array configuration over an ion exchange membrane include physical rigidity and strength. Due to the ball-in-seat check valve type of configuration, an excellent seal is formed between the bead seat cavities and the resin beads. The array of beads would be suitable for applications that presently use ion exchange membranes such as eluent-generator suppressors, electrodialysis-based water purifiers and the like.

Figure 4A:
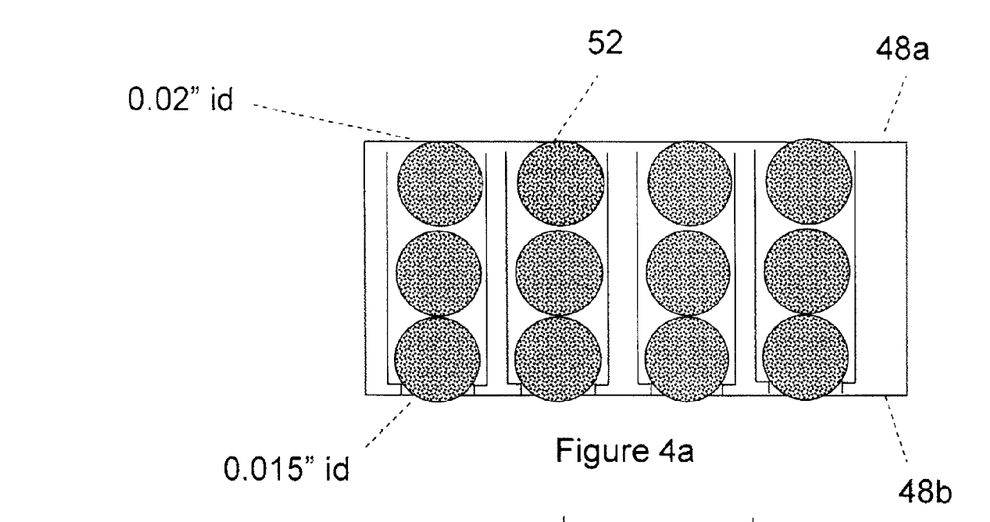
FIG. 4a is a side view of a bead array barrier.
Figure 4B:
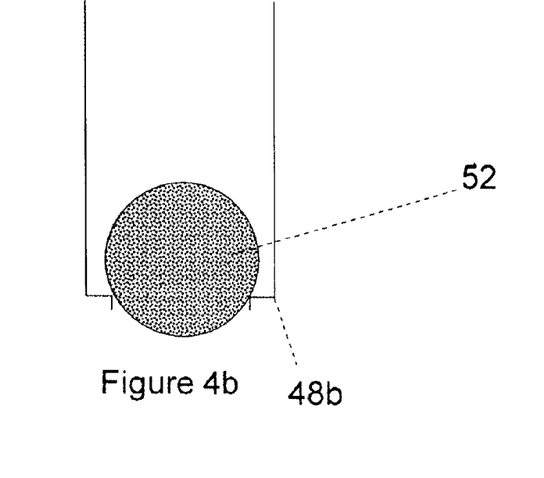

In some embodiments of the bead array, a single ion exchange bead is in fluid communication with fluid in the chambers on opposite sides of the bead. In other embodiments, such as illustrated in FIGS. 4a and 4b, two or more ion exchange beads are stacked in a tandem line extending between fluids in the two chambers. Here, a first bead is in fluid communication with a first chamber and a second bead is in fluid communication with a second chamber. Intermediate beads can be interposed between the first and second beads. The tandem beads contact each other and provide a continuous ion transport path between the first and second chambers. In all of these embodiments, the ions are transported from the first chamber to the second chamber through at least one ion exchange bead.

In another embodiment, a reverse electrical bias may be applied in the system of the present invention. A potential is applied in the reverse direction of the current normally applied to generate the eluent. Under normal conditions, when an electrolyte is placed at a high concentration on one side of an ion exchange bead or membrane and when water flows on the other side of the membrane, a small leakage of the electrolyte into the water occurs because of the high concentration gradient, even though the passage of one type of ion, of charge similar in sign to the fixed charges in the membrane, are inhibited due to the Donnan potential. For example when a KOH eluent generator is operated with feed KOH separated by a cation exchange membrane from a recipient water stream, the KOH concentration in the product stream increases linearly with the current applied (with KOH side containing the positive electrode and the water side containing the negative electrode) in accordance with Equation 3. However, even when no current is applied, the exit stream contains a finite nonzero amount of KOH. When an eluent is generated, this leakage affects the total concentration generated. By applying a current in the reverse direction, i.e., by holding the KOH reservoir side negative and the water side positive, this undesired leakage can be greatly minimized.

An eluent generator that can produce nearly pure water when demanded (i.e. water containing less KOH than would be leaking out under no-voltage applied conditions) and also produce high KOH concentrations when demanded can be provided with a bipolar variable voltage power supply which contains at least two electrodes one being held at ground potential and connected to the water side while the second electrode, whose potential can vary continuously from a negative value with respect to the said ground electrode to a positive value with respect to the said ground electrode is deployed on the feed KOH side. In operation, when it is desired to vary the eluent composition from nearly pure water to relatively high concentration of KOH, the potential of the electrode on the KOH side is varied, continuously if desired, from a negative value to a positive value.

In an alternative embodiment, one may use a three terminal bipolar variable voltage power supply, often called a variable dual power supply where terminal 1 is maintained at ground potential, terminal 2 can assume any potential from 0 to +15 V with respect to terminal 1 and terminal 3 can assume any potential from 0 to −15 V with respect to terminal 1. In the generator, one of the electrodes is connected to terminal 1. The other electrode is connected to either terminal 2 or terminal 3 as selected by an automated relay, which is switched at the appropriate time.

The bipolar variable voltage power supply of the prior paragraph is a single power supply capable of applying two voltages of opposite polarity to a pair of electrodes so that two different voltages of opposite polarity can be applied in a programmed manner. This is referred to as the reverse electrical bias embodiment. In another embodiment, two independent power supplies can perform this reverse polarity function. As used in the reverse electrical bias context, the term "power supply" refers to both a single power supply and two or more independent power supplies that perform these dual functions.

The above system has been described with respect to an eluent generator. However, it is applicable to the substitution of the seated ion exchange bead barrier for ion exchange membranes in other ion transport apparatus and method. For example, in a suppressor in an ion chromatography system such as illustrated in U.S. Pat. No. 5,352,360, the ion exchange bead is substituted for the ion exchange membrane. (However, the reverse electrical bias embodiment may not be applicable to a suppressor.) The KOH solution illustrated in FIGS. 1 and 2 herein can comprise the liquid sample stream containing the electrolyte to be suppressed exiting from the chromatographic column 10 in FIG. 1 of the '360 patent. The solution on the other side of the ion exchange beads 28*a* and 28*b* may comprise a regenerant solution (e.g. water for an electrolytic suppressor) which flows on the other side of the ion exchange membrane from the liquid sample stream in the '360 patent.

In other embodiments, not shown, the ion source can be fed to the ion source chambers without flowing through electrode tubes. Further, the ion source chamber can be a substantially non-flowing solution, such as illustrated in the large-capacity reservoir of U.S. Pat. No. 5,352,360. For this embodiment, the bead array approach is particularly effective. Also, the ion exchange bead approach is applicable to a non-electrolytic ion transport device and method which does not use electrodes. Note that a bead array does not have to be a one dimensional array (1×n); rather it can be a multidimensional array where mn beads are deployed in a m×n array.

EXAMPLE 1

The design in FIG. 1 is made from a commercial cross fitting and the data are based on this device. The through-channels of both arms of a 10-32 cross fitting (P-730, Upchurch) were bored out for 1/16 in. o.d. PEEK tubing to just pass through. For each of two segments of 0.020 in i.d., 1/16 in. o.d. PEEK tubing, the terminal bore at one end was widened to 0.9 mm (0.035 in.) to a depth of ~1 mm. Ion exchange resin beads (Rexyn 101H$^+$-type for the cation exchange resin (CER) and Dowex AG-2X8 Cl$^-$-form for the anion exchange resin (AER)) were dried in a desiccator and hand-picked to obtain resin beads in the 0.8-0.85 mm size range. One CER and one AER bead were placed in the respective drilled out cavities in the PEEK tube and wetted with water whereupon they expanded and lodged tightly in the cavity. As shown in FIG. 1, these two bead-bearing tubes were placed opposite each other and fixed in place with 10-32 nuts and ferrules, water inlet and eluent outlet tubes were then similarly connected. At the back side, each bead-bearing tube was cut off essentially flush with the back of the holding nuts and a small segment of Tygon sleeve tubing put over the ends of the 1/16 in. o.d. PEEK tubes. A blunt-ended platinum needle (0.25 mm i.d., 0.45 mm o.d.; 26 ga., 1 in. long, P/N 21126 PT 3, Hamilton Co. Reno, Nev.) was put in all the way into the PEEK tubing, (almost) touching the bead. The exit of the Pt Needle from the Tygon tube was sealed with hot-melt adhesive. The Pt-needle functioned both as the electrode and the liquid inlet tube; the liquid outlet was provided by a 0.25 mm. i.d., 0.51 mm o.d. PEEK tube (P/N 1542, Upchurch) breaching the Tygon tube wall, and affixed in place with adhesive. The nominal internal volume of this generator, without considering the space that the protrusion of the spherical beads may consume, the volume is ~3.2 µL.

EXAMPLE 2

A high pressure capillary IC system consisted of a high pressure syringe and a high pressure header valve (P/N 23994 and 26098, Kloehn) connected to a flow-through pressure sensor (SP70 A-3000, www.senso-metrics.com) via 0.25 mm i.d., 1.6 mm o.d. PEEK tubing. The stream passes through the high pressure generator, as described above. Unless otherwise stated, in the generator, 100-200 mM KOH was used for feeding both electrode chambers. The reservoir was pressurized at 12 psi (the pneumatic line contained a soda lime trap to prevent intrusion of $CO_2$ into the liquid) and this was sufficient to establish a flow of ~500 μL/min each through both anode and cathode chambers. The effluent could in principle be recycled but this was not presently carried out. The injection volume was 200 nL. A chromatographic flow rate of 3.2 μL/min was used throughout otherwise stated. The generator output proceeded through a first conductivity cell consisting of two 4.5 cm long, 0.25 mm bore, 1.6 mm o.d. stainless steel (SS) tubes joined by a 10-32 PEEK union with the gap between the two SS tubes being ~1 mm). The SS tubes functioned as flow-through electrodes connected to bipolar pulse conductivity detection electronics (CDM-1, Dionex Corp.). The conductance calibration data were used to translate measured conductance values to KOH concentration. This detector output was thus used to measure the generated KOH concentration.

A monolithic anion exchanger column (housed in a 0.25 mm i.d.×0.365 mm o.d.×260 mm long fused silica capillary) used in this work utilized a sulfonated functionality acrylate cation exchanger as a starting point. This was converted to an anion exchanger by pumping a colloidal solution of anion exchanger nanoparticles (AS18 latex, Dionex Corp.) until no further retention of the latex was apparent.

Alternatively, silica capillary columns, 50 μm and 75 μm in i.d., each 5-m long, were coated with AS-11 anion exchanger latex nanoparticles supplied by Dionex Corp. Briefly, we used a Kloehn V6 syringe pump (www.Kloehn.com) with a 1 mL glass syringe to pump water into the generator, typically at 0.5-1.5 μL/min. The anode compartment of the generator was fed with 10-20 mM (10 mM if not otherwise specified) KOH by a peristaltic pump. The cathode compartment was fed independently with the same liquid or with pure water. In this case a 20 mL loop volume internal loop sample injector was used.

The column effluent passed through a tubular Nafion membrane suppressor regenerated by 10 mM $H_2SO_4$) into a contactless conductivity detector. This detector was calibrated to function in a low conductivity range and to thus measure analyte signals. As detector electrodes, two tubular SS segments (0.41 mm i.d.×0.66 mm o.d.×15 mm long) were affixed with epoxy adhesive directly on the silica capillary exiting the suppressor, with a 1 mm interelectrode gap. The electrodes were coupled to an AD7746 (www.analogdevices.com) capacitance to voltage digital converter evaluation board and then forms a complete contactless conductance detector, in which the measured signal is proportional to the solution conductance in the low conductance domain relevant to this work.

Water used was distilled and deionized with a specific resistivity≧18.2 MΩ·cm. All experiments were carried out at laboratory temperature of 22±1° C.

EXAMPLE 3

Figure 3A:
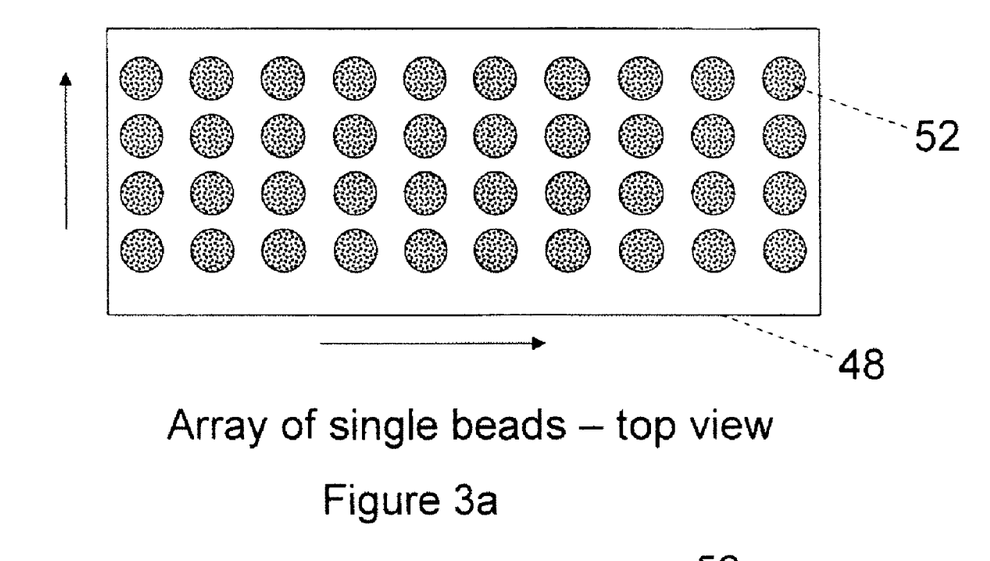
FIGS. 3a and 3b are top and side views, respectively, of a bead array barrier according to the present invention.
Figure 3B:
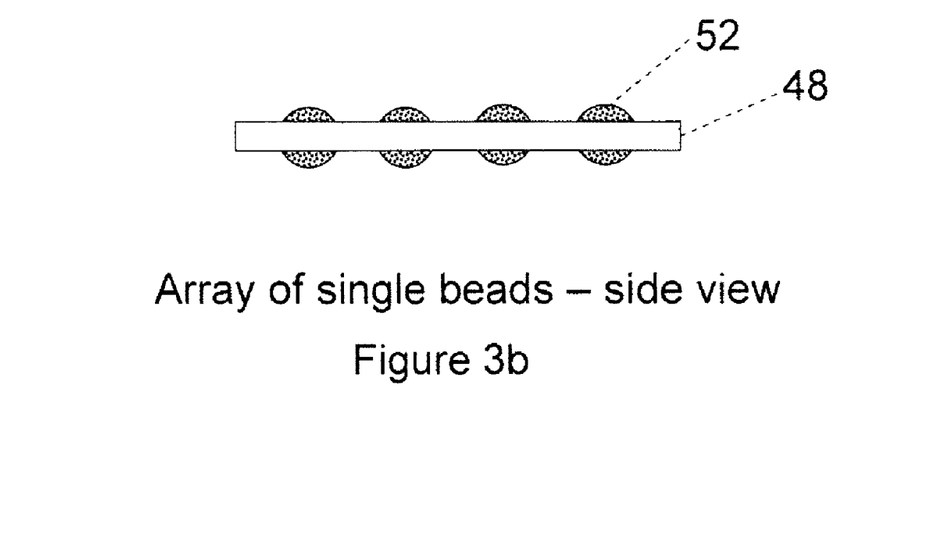

This example illustrates the bead array of FIGS. 3a and 3b. A polypropylene sheet (48) of a thickness of 0.015" (381 microns) was drilled out mechanically with an array of 0.02" (508 microns) diameter holes (50 not shown) which constituted the bead seat. Referring to FIGS. 3a and 3b, cation exchange resin beads (52) purchased from Rohm & Haas and sold as Amberjet UP1400 semi conductor grade cation exchange resin, were sized to barely fit the 508 micron hole. The ion exchange resin bead is in the dry form during this step. Upon hydrating the membrane with de-ionized water there is sufficient expansion of the resin bead allowing a tight fit with the outer diameter of the hole or bead seat. The net result is the ion exchange resin beads are seated on a flat surface wall as shown in FIG. 3a) top view and FIG. 3b (side view). This membrane when exposed to DI water or acid did not show any bulk dimensional change as per the present invention and is suitable for use in a ASRS suppressor as a cation exchange membrane.

EXAMPLE 4

This example illustrated the bead area of FIGS. 4a and 4b. A thicker version of the polypropylene sheet from Example 3 (0.06" in thickness) was drilled with multiple conduits of 0.02" id from the surface 48a and up to a depth of 0.055". The bottom of the conduit was opened on the 48b surface to a dimension of 0.015" to create a bead seat. Dry cation exchange resin from Example 3 was used to pack the conduit, three beads in each conduit. The finished product is a thick cation exchange membrane similar to the membrane shown in Example 3. The resin in the bottom layer is held in place against the bead seat and forms a seal. Appropriate backing such as a polypropylene screen (not shown) can be placed along the surface 48a to ensure that the resin beads are held in place. Any flow of liquid along the surface 48a will force the cation exchange beads against the surface at 48b thus forming a high pressure seal as per the present invention. An enlarged view of the resin bead seat sealing interface is shown in FIG. 4b. This membrane is suitable for assembly in an ASRS suppressor device and replaces the cation exchange membrane.

Results and Discussion

Eluent production at zero current has been largely attributed to Donnan forbidden leakage but the mechanism through which this occurs has not been established. In the following experiments with the generator of FIG. 1, the leakage was 107 pmol KOH/s whether (a) 4 M KOH was present both in the cation exchange resin (CER) and the Anion Exchange Resin (AER) compartments (26a and b) or (b) just the CER compartment contained 4 M KOH, the AER chamber containing pure water. In contrast, when the CER chamber contained only water and the AER chamber contained 4 M KOH, the OCP was far less, only 3-4 pmol KOH/s. Obviously, it is processes at the CER bead that dominantly govern the observed leakage. There is no compelling reason why one type of ion exchange resin will be more susceptible to Donnan-forbidden leakage than another; so it is not logical that Donnan-forbidden leakage occurs through the CER bead but not the AER bead. However, a cation exchange process can take place between a $K^+$-laden CER bead and $H^+$ in the flowing water, leading to KOH formation in the water. In contrast, exchange of $OH^-$ from an $OH^-$-laden AER bead with $OH^-$ in water will lead to no observable change. Although it may seem that the likelihood of the $K^+$-$H^+$ exchange process is low because of very low concentrations of $H^+$ in water, it has also been known for a long time that the effective selectivity factor for an ion increases when it is present in very low concentration.

Figure 5:
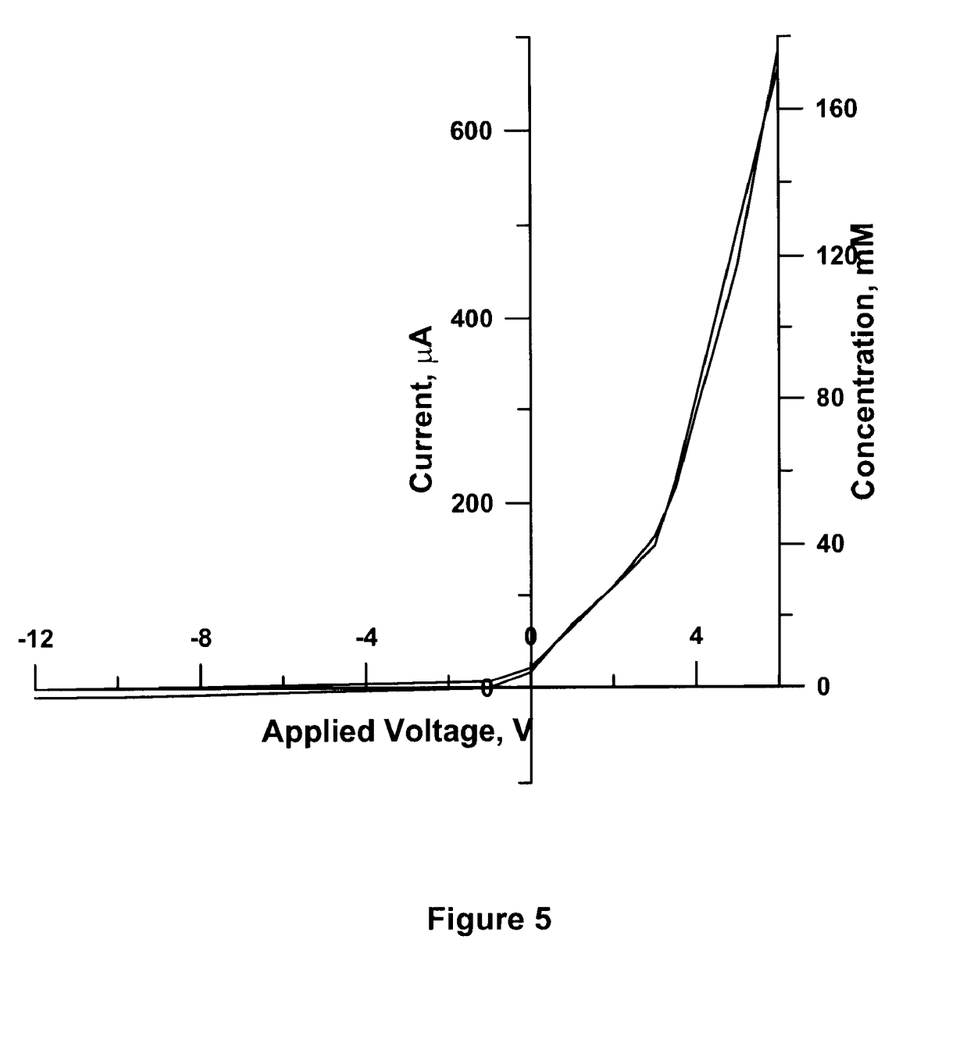
FIG. 5 is a graph showing current-voltage-concentration behavior of high pressure bead-based electrodialytic generator, 4 M KOH in both cathode and anode chambers.

FIG. 5 shows plots for both current-voltage and applied voltage vs. generated KOH concentration for the resin bead based generator of FIG. 1 with 4 M KOH in both CER and AER chambers. In this case, the applied voltage spans from negative to positive. In these devices, significant current pass only when the polarity is such that the electric field aided induced ion transport is permitted by the respective exchangers. This is analogous to the behavior of a semiconductor diode but the current through the device is carried by ionic transport. A small negative current is generated under negative applied voltage (KOH feed side negative with respect to water receiving side); this exhibits a much smaller slope than the positive i-V slope when the applied voltage is +ve. To attain a zero current level, a bias of approximately −1 V is needed under these specific conditions.

For positive applied voltages, the generated KOH concentration is linearly related to the current regardless of the generator design. In FIG. 5, we deliberately chose ordinate scaling such that the current and concentration traces will be seen to be nearly superimposed in the positive applied voltage region.

The minimization of leakage by applying reverse voltage to the generator is important because this assures that the generator can generate near-zero KOH concentrations when sufficient reverse voltage is applied. Although these data are present in FIG. 5, it is not easy to exactly discern the generated KOH concentration at high negative potentials. For the generator of FIG. 1 with both electrode compartments containing 4 M KOH and water flowing between at 4 μL/min, one may begin with −12 V applied to the CER side electrode with respect to the ground electrode on the AER side, whence the KOH concentration observed in the exit stream is observed to be near zero (0.03 mM). When this voltage is swept up to ~+5V, the generated KOH concentration is observed to be 130 mM, a change of more than 4000×.

A major advantage of the resin beads approach is their ability to function as robust ball-in-seat check valves. To assure ample mechanical strength of the exchange bead, we only worked with resin beads with a crosslinking of 8% and higher, it is well known that beads with up to 50% crosslinking have been prepared. The second factor is to assure the seal between the ball and the seat. As long as we picked beads with no observable surface imperfections or cracks as observed under a low magnification microscope, no problems were encountered. The ability to withstand high-backpressure and leakage from the generator chamber out was explored. The EDG was connected to a column that generated a backpressure of 1400 psi (the highest rated pressure for the syringe header valve was 1500 psi) at the programmed syringe flow rate of 7 μL/min. The terminal flow in the system was measured with and without the column. During this period the EDG was not operated (i.e., no voltage was applied) and we also measured any leakage of fluid through the capillaries in the electrode chambers over 30 min long periods. There was no observable leakage.

Figure 6:
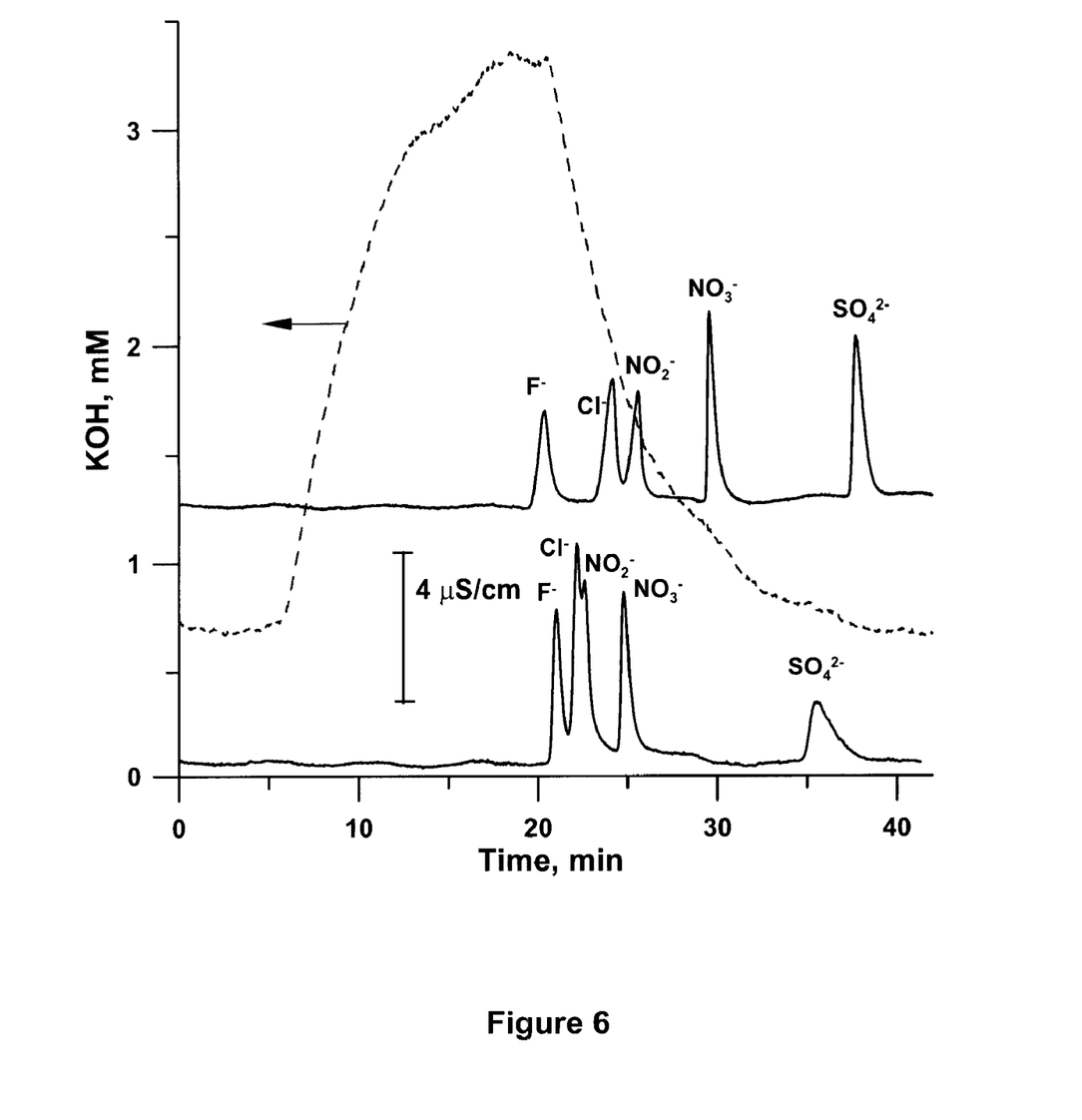
FIG. 6 is a chromatogram performed by low-pressure planar membrane eluent generator, 10 mM KOH anode feed, cathode feed water. 75 μm×5 m fused silica column coated with AS 11 latex, flow rate 1.5 μL/min. Sample 200 picoequivalents of each anion in 20 nL. Lower chromatogram isocratic, 2.1 mM KOH eluent. Actual gradient profile for upper gradient chromatogram is shown in the figure.
Figure 7:
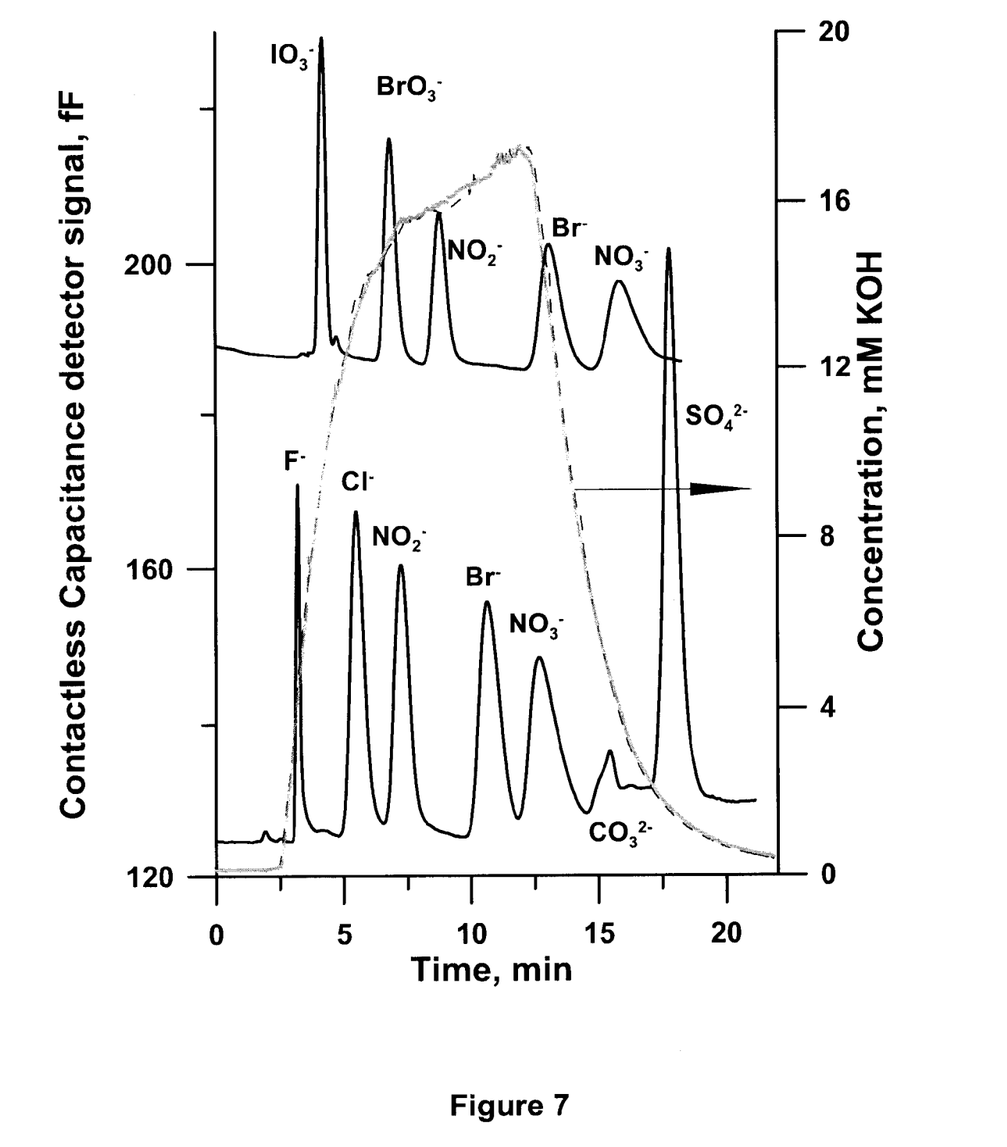
FIG. 7 shows isocratic (top, 5.5 mM KOH, 3.2 μL/min) and gradient (bottom) chromatograms on a monolithic AS-18 latex coated ion exchanger (0.25×260 mm, ΔP=400 psi). Two repeats of a gradient profile are shown in the inset. KOH was present in both cathode and anode chambers. Detector background rose by 11 fF during the run and was subtracted. Injection volume 200 nL; Top: 200 pmol of each ion; bottom: 100 pmol for $F^-$, 300 pmol for others, carbonate was not deliberately added.

Isocratic and gradient chromatograms obtained with the bead based EDG on a packed capillary are shown in FIGS. 6 and 7. The inset also shows the repeatability of a gradient profile. Retention time reproducibility ranged from 0.6-1.2% (detailed data are presented in Table 1) under isocratic conditions; these are comparable to the reproducibility of flow rate of the present pumping system. The reproducibility varied between 0.3% and 1.5% under gradient elution conditions for all ions except for fluoride. Elution of fluoride is very sensitive to the eluent remaining in the column from the previous cycle; the retention time reproducibility for fluoride under gradient conditions was 3.0%.

A rapid increase in the eluent concentration is often desired in gradient IC. At the operational flow rate of 5 μL/min, the 10%-90% rise time was ~1.3 min, the 90-10% fall time was much longer at ~8 min; however experiments show that this can be reduced by applying reverse voltage. As previously observed, when the EDG current is abruptly stepped down, a small transient increase in the eluent concentration occurs before the concentration decreases.

In summary, we have shown here for the first time that in regard to ionic transport, the behavior of these devices fully corresponds to that of a semiconductor diode. Reverse bias can be applied to minimize electrolyte leakage or ion exchange. For the resin bead devices, there is also a unique mechanical advantage: The spherical shape of ion exchange resin beads make them ideal candidates for miniature "ball-on-seat" valves, thus making fabrication of high pressure devices in a miniature format simple, very different from the sealing problems intrinsic to any high pressure device that must contain a membrane. We have found that they work reliably over long periods. We have also observed that with appropriate type of ion exchanger, nature of electrolyte in the electrode compartment and electrode polarity chosen, such devices can be used as "suppressors" or "deionizers". Indeed, a generator operating under reverse bias is functionally operating as a deionizer where any electrolyte leaking out is being electrically aspirated back out.

What is claimed is:

1. Ion transport apparatus in which ions of one charge, positive or negative, in a first chamber are transported to a liquid in a second chamber through a first barrier which substantially blocks bulk liquid flow between the first and second chambers, said apparatus comprising:
    (a) a first chamber and an adjacent second chamber having an inlet spaced from an outlet, said first and second chambers being capable of simultaneously retaining a liquid and
    (b) a first barrier separating said first and second chambers, said first barrier substantially blocking bulk liquid flow between the first and second chambers, said first barrier comprising a first wall and a first ion exchange bead sealed in a first bead seat in said first wall, said first ion exchange bead being capable of passing ions of one charge, positive or negative, and of substantially blocking bulk liquid flow.

2. The ion transport apparatus of claim 1 in which said first ion exchange bead is in fluid communication with said first chamber.

3. The ion transport apparatus of claim 2 in which said first ion exchange bead is in fluid communication with said second chamber.

4. The ion transport apparatus of claim 1 in which said second chamber is of elongate generally tubular configuration.

5. The ion transport apparatus of claim 1 in which said second chamber is a capillary conduit.

6. The ion transport apparatus of claim 1 further comprising a first source of aqueous liquid in fluid communication with said first or second chamber.

7. The ion transport apparatus of claim 1 further comprising a first electrode in electrical communication with said first chamber.

8. The ion transport apparatus of claim 7 further comprising a second electrode in electrical communication with said second chamber.

9. The ion transport apparatus of claim 8 further comprising a power supply for applying an electrical potential across said first and second electrodes.

10. The ion transport apparatus of claim 9 in which said power supply is capable of applying a first voltage between said first electrode and second electrode at a first polarity and of applying a second voltage of a second polarity opposite to said first polarity.

11. The ion transport apparatus of claim 1 further comprising (c) a third chamber capable of simultaneously retaining a liquid adjacent said second chamber, and (d) a second barrier separating said third chamber from said second chamber and being spaced apart from said first barrier, said second barrier substantially blocking bulk liquid flow and comprising a second wall and a second ion exchange bead sealed in a second bead seat in said second wall, said second ion exchange bead being in fluid communication with said second and third chambers and being capable of passing ions of one charge, positive or negative, and of substantially blocking bulk liquid flow.

12. The ion transport apparatus of claim 11 further comprising (e) first and second electrodes in electrical communication with said first and third chambers.

13. The ion transport apparatus of claim 12 comprising an electrolytic eluent generator.

14. The ion transport apparatus of claim 11 in which said first and second ion exchange beads have the same charge, positive or negative.

15. The ion transport apparatus of claim 11 in which said first and second ion exchange beads are of opposite charge, positive or negative.

16. The ion transport apparatus of claim 1 comprising a suppressor.

17. The ion transport apparatus of claim 1 including a plurality of ion exchange beads in addition to said first bead and of the same charge as said first bead, positive or negative, sealed in a plurality of bead seats in said first wall.

18. A suppressor for ion chromatography comprising:

(a) an ion receiving flow channel and an adjacent liquid sample flow-through channel having an inlet spaced from an outlet, said ion receiving flow channel and sample flow-through channel being capable of simultaneously retaining a liquid, and (b) a first barrier separating said ion receiving flow channel and said sample flow-through channel, said first barrier substantially blocking bulk liquid flow between said ion receiving flow channel and said sample flow-through channel and comprising a first wall and a first ion exchange bead sealed in a bead seat in said first wall, said first ion exchange bead being in fluid communication with said ion receiving flow channel, and being capable of passing ions of one charge, positive or negative, and of substantially blocking bulk liquid flow.

19. The suppressor of claim 18 further comprising (c) a second chamber, said first and second chambers being capable of simultaneously retaining a liquid, adjacent said liquid sample stream flow-through channel, and (d) a second barrier separating said second chamber from said sample flow-through channel and being spaced apart from said first barrier, said second barrier substantially blocking bulk liquid flow and comprising a second wall and a second ion exchange bead sealed in a bead seat in said second wall, said second ion exchange bead being in fluid communication with said second chamber and said sample flow-through channel and being capable of passing ions of one charge, positive or negative, and of substantially blocking bulk liquid flow.

20. The suppressor of claim 18 in combination with a chromatographic separator, said chromatographic separator being in fluid communication with said sample flow-through channel inlet.

21. Apparatus for electrolytically generating an acid, a base, or a salt comprising:

(a) a first chamber and an adjacent eluent generation flow-through channel having an inlet spaced apart from an outlet, said eluent generation flow-through channel being capable of simultaneously retaining a liquid, (b) a first barrier separating said first chamber and said eluent generation flow-through channel, said first barrier substantially blocking bulk liquid flow between the first and second chambers, said first barrier comprising a first wall and a first ion exchange bead sealed in a bead seat in said first wall, said first ion exchange bead being capable of passing ions of one charge, positive or negative, and of substantially blocking bulk liquid flow, and (c) first and second electrodes in electrical communication with said first chamber and eluent generation flow-through channel, respectively.

22. The transport apparatus of claim 21 in combination with a chromatographic separator, said sample stream flow channel outlet being in fluid communication with said chromatographic separator.

23. The apparatus of claim 21 further comprising (c) a second chamber adjacent said eluent generation flow-through channel, and (d) a second barrier separating said eluent generation flow-through channel from said second chamber and being spaced apart from said first barrier, said second barrier substantially blocking liquid flow and comprising a second wall and a second ion exchange bead sealed in a bead seat in said second wall, said second ion exchange bead being in fluid communication with said second chamber and said eluent generation flow-through channel and being capable of passing ions of one charge, positive or negative, and of substantially blocking bulk liquid flow.

24. A method which includes transporting ions of one charge, positive or negative, in a liquid in a first chamber to liquid in a second chamber through a barrier which blocks bulk liquid flow between the first and second chambers, said method comprising:

(a) providing a first ion source in a liquid containing a selected ion of one charge, positive or negative, in a first chamber, (b) flowing an ion receiving liquid stream through an ion receiving flow channel adjacent said first chamber, (c) providing a first barrier separating said first chamber from said ion receiving flow channel, said first barrier substantially blocking bulk liquid flow between the first and second chambers, said first barrier comprising a first wall and a first ion exchange bead sealed in a bead seat in said first wall, said first ion exchange bead being capable of transporting ions of one charge, positive or negative, and of substantially blocking bulk liquid flow, (d) transporting said selected ion from said ion source to said flowing ion receiving stream through said first ion exchange bead, (e) providing a second chamber including an aqueous liquid adjacent said ion receiving flow channel, and (f) providing a second barrier separating said second chamber from said ion receiving flow channel, said second barrier substantially blocking bulk liquid flow and comprising a second wall and a second ion exchange bead sealed in a bead seat in said second wall, said second ion exchange bead being capable of transporting ions of one charge, positive or negative, and of substantially blocking bulk liquid flow in fluid communication with said second chamber.

25. The method of claim 24 in which a first electrical potential is passed between a first electrode in electrical communication with said first chamber and a second electrode in electrical communication with said ion receiving flow channel.

26. The method of claim 25 in which a second electrical potential of opposite polarity to said first electrical potential is passed between said first electrode and said second electrode.

27. The method of claim 24 further comprising passing a current between said ion source in said first channel and said ion receiving flow channel though said first ion exchange bead.

28. A method of suppressing a liquid for ion chromatography comprising:
   (a) providing an ion receiving flow channel and an adjacent liquid sample flow-through channel having an inlet and an outlet,
   (b) providing a first barrier separating said ion receiving flow channel and said sample flow-though channel, said first barrier substantially blocking bulk liquid flow between said ion receiving flow channel and said sample flow-through channel and comprising a first wall and a first ion exchange bead sealed in a bead seat in said first wall, said first ion exchange bead being capable of passing ions of one charge, positive or negative, and of substantially blocking bulk liquid flow,
   (c) flowing a sample solution including sample ions of one charge, positive or negative, which have been chromatographically separated in an eluent including selected ions of opposite charge to said sample ions through said liquid sample flow-through channel, and
   (d) suppressing said eluent selected ions by transporting said selected ions from said sample stream flow channel through said first ion exchange bead into said ion receiving flow channel.

29. The method of claim 28 further comprising passing a current between said sample stream flow channel and said ion receiving flow channel though said first ion exchange bead.

30. An electrolytic method for generating an acid or a base comprising:
   (a) providing an anion or a cation source in an aqueous liquid in an anion or cation source reservoir in a first chamber,
   (b) flowing an aqueous liquid stream through an acid or base generation chamber separated from said anion or cation source reservoir by a first wall separating said first chamber and said acid or base generation flow-through channel, said first wall comprising a first ion exchange bead sealed in a bead seat in said first wall, said first ion exchange bead being capable of passing ions of one charge, positive or negative, and of substantially blocking bulk liquid flow,
   (c) applying an electrical potential between said anion or cation source reservoir and said acid or base generation chamber, respectively, through said ion exchange bead, and
   (d) transporting said anion or cation from said anion or cation source reservoir through said first ion exchange bead into said acid or base generation chamber to electrolytically generate an acid, base, or salt.

* * * * *